United States Patent [19]

Demetrescu

[11] 4,323,079

[45] * Apr. 6, 1982

[54] APERIODIC ANALYSIS SYSTEM, AS FOR THE ELECTROENCEPHALOGRAM

[75] Inventor: Mihai C. Demetrescu, Irvine, Calif.

[73] Assignee: The Regents of the University of California, Berkeley, Calif.

[*] Notice: The portion of the term of this patent subsequent to Aug. 5, 1997, has been disclaimed.

[21] Appl. No.: 107,204

[22] Filed: Dec. 26, 1979

Related U.S. Application Data

[62] Division of Ser. No. 973,423, Dec. 26, 1978, Pat. No. 4,215,697.

[51] Int. Cl.³ .............................................. A61B 5/04
[52] U.S. Cl. ..................................................... 128/731
[58] Field of Search ......................................... 128/731

[56] References Cited

U.S. PATENT DOCUMENTS

| | | | |
|---|---|---|---|
| 3,495,077 | 2/1970 | Hiltz et al. | 128/731 |
| 3,513,834 | 5/1970 | Suzuki et al. | 128/731 |
| 3,548,812 | 12/1971 | Paine | 128/731 |
| 3,621,836 | 11/1971 | Nagatomi | 128/731 |
| 3,809,069 | 5/1974 | Bennett | 128/731 |
| 3,848,586 | 11/1974 | Suzuki et al. | 128/731 |

OTHER PUBLICATIONS

Dascalov et al., Medical & Biological Engineering, v. 12, No. 3, May 1974, pp. 335–338.
Kalocay, "Biomedizinsche Technik", v. 21, No. 5, Jun. 1976, pp. 140–143.
Colburn, Medical & Biological Engineering, v. 12, No. 2, Mar. 1974, pp. 194–198.

Primary Examiner—William E. Kamm
Attorney, Agent, or Firm—Nilsson, Robbins, Dalgarn, Berliner, Carson & Wurst

[57] ABSTRACT

An aperiodic signal is preliminarily processed by an active network to provide three relatively separate components that include: slow waves (waveform cycles or fragments of equivalent frequency from 1 to 8 hertz), fast waves (waveform cycles or fragments of equivalent frequency from 8 to 30 hertz), and a signal component which may contain spikes (fast, large, sharp single waves). The component signals or waves are applied to individual detector circuits which indicate amplitude and period (or equivalent frequency) information for detected waves and the amplitude for recognized spikes, as well as the time of their occurrence. Detected waves (including spikes) produce representative trigger signals which are applied through a multiplexer to a storage device, specifically a cathode ray tube on which the waves and spikes are representatively displayed and stored to complete a static picture which indicates an interval of the waveform. As disclosed, a representation or picture is generated on the storage tube by controlling the horizontal and vertical amplifiers and appropriately blanking the beam to develop a composite display that summarizes many seconds of the aperiodic signal. The display is a three-dimensional representation with each wave represented by a line that extends in one dimension to indicate amplitude. The position of the line in another dimension indicates the period or equivalent frequency, and its position in the third dimension indicates the time of occurrence of the wave.

7 Claims, 10 Drawing Figures

APERIODIC ANALYSIS SYSTEM, AS FOR THE ELECTROENCEPHALOGRAM

This is a division of Application Ser. No. 973,423, filed Dec. 26, 1978, now U.S. Pat. No. 4,215,697, issued Aug. 5, 1980.

BACKGROUND AND SUMMARY OF THE INVENTION

The electroencephalogram (EEG) is essentially a waveform that is representative of electrical variations occurring between distinct locations on the human head. Characteristically, the EEG is a non-periodic, stochastic phenomenon. That is, oscillations in the electrical potential cannot be predicted, consequently only current and past information is available. The absence of recurring patterns in the waveform considerably complicates analysis of the EEG, as for use in diagnosis. However, in spite of the fact that the techniques are neither simple nor easy, neurologists have established principles and criteria for utilizing the EEG as an effective diagnostic tool.

In general, the EEG may be displayed either in a transitory manner (as on a cathode ray tube) or as a permanent record in the form of a strip chart. The cathode ray display of such waveforms is so transient that even an expert may have difficulty making an accurate analysis. As for a strip chart or paper record, the useful information can be extracted from the EEG only by recording at plotting speeds which result in a considerable volume of paper, e.g. 180 pages per hour. Essentially, the density of useful information in EEG records is low; and direct examination is laborious and time consuming.

A substantial part of the training of an EEG specialist consists of developing the ability to quickly recognize characteristic waves and patterns and to evaluate amplitude and frequency without the use of instruments. The demanded concentration for manually analyzing an EEG, along with other considerations, has resulted in various efforts to more efficiently decode and concentrate EEG information. In that regard, concurrent efforts have also been made to reduce the degree of expertise necessary for extracting useful information from the EEG. However, a need has long existed for a system to provide a more compact, simplified format for an EEG.

Over a considerable period of time, beginning in the 1930's and with no end in sight, several proposed methods of decoding and concentrating EEG information relied on Fourier analysis and primarily are referred to as "power spectra". Essentially, the basis of such techniques is the utilization of the Fourier transform to dissect the complex EEG waveforms on the basis of frequency into a plurality of component signals. The approach involves several objections, one of which relates to the inherent nature of the EEG as an aperiodic waveform.

The principal result of a Fourier-type analysis is to reveal and measure harmonics; however, there is no recognized significance of the higher order harmonics of the EEG. Also, the temporal sequence of the EEG events disappears as a result of the "averaging" operation which cannot be disassociated from the analysis in utilizing classical techniques. A single spectrum results from the analysis of several seconds of the EEG signal and (even if it represents correctly the total energy at a given frequency) it cannot show temporal distribution between waves or coincidence of typical elements. For instance, the simultaneous occurrence of spikes and slow waves in a classic "spike and wave" pattern is essential for the diagnosis of PM epilepsy. Harmonic analysis, however, even if it could signal the presence of spikes, could not ascertain their simultaneous occurrence with the slow wave.

Other examples can be found in characteristics of certain EEG waves known as "spindles", the EEG arousal, the K-complex, and so on, where the temporal sequence is significant. Single isolated events such as EEG spikes do not influence significantly the result of harmonic analysis and are not indicated in the power-frequency spectrum generally resulting from Fourier-type analysis.

In summary, it is the amplitude (voltage) of the EEG waveform (and not the energy or power content) which is significant for diagnosis and analysis. Short-duration waves (waveform components) of relatively large amplitude contain little energy but are highly significant.

In spite of the problems suggested above in analyzing EEG information by Fourier analysis techniques, substantial work has been done some of which is mentioned in a book, *Monitoring in Anesthesia,* edited by L. J. Saidman and N. T. Smith, published by John Wiley & Sons, Inc., 1978. The reference also refers to the work of the present development.

Considering the need for improved techniques in analyzing EEG information, an initial aspect involves devising a format for condensing the data represented by the aperiodic EEG waveform. In that regard, the present inventor initially devised a format to present EEG information in a concentrated form while preserving individual characteristics of the waves. The format was described in *The Physiologist,* Volume 18, No. 3, August 1975. In accordance with the format, the EEG is translated to a form which preserves the characteristics traditionally recognized by neurologists in analyzing EEG's. The waveform was considered as containing meaningful fluctuations defined either as spikes or certain waves classified in accordance with amplitude and duration as aperiodic transitory events. In accordance with the format of representation, the amplitude of waves and spikes is depicted as the height of an L-shaped character shown in a three-dimensional reference system where equivalent frequency is indicated on the horizontal and time is referenced on the depth axis. Utilizing such a format, it appeared that up to 180 seconds of EEG recording could be represented on a single page without loss of traditionally important information.

In general, the present invention is directed to a system whereby EEG information is decoded and presented in a concentrated format indicated above, so as to preserve the individual characteristics of the waves or waveform components. In that sense, the characteristics of the waveform which have been important for classic and traditional wave analysis are preserved in the display.

BRIEF DESCRIPTION OF THE DRAWINGS

In the drawings, which constitute a part of this specification, an exemplary embodiment, demonstrating the various objectives and features hereof, is set forth as follows.

DESCRIPTION OF THE ILLUSTRATIVE EMBODIMENT

As indicated above, a detailed illustrative embodiment of the invention is disclosed herein. However, systems for aperiodic analysis may be embodied in accordance with various forms, some of which may be detailed rather differently from the disclosed embodiment. Consequently, the specific structural and functional details disclosed herein are merely representative, yet in that regard they are deemed to afford the best embodiment for purposes of disclosure and to provide a basis for the claims herein which define the scope of the present invention.

Figure 1:
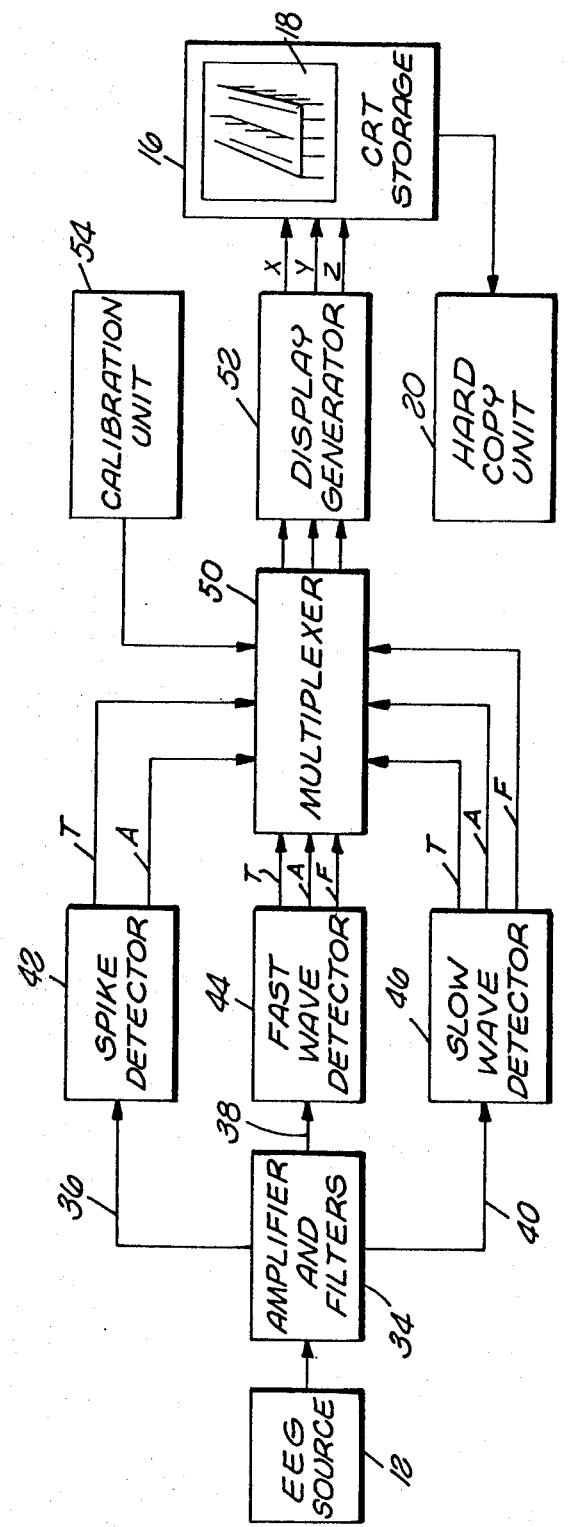
FIG. 1 is a block diagram of a system constructed in accordance with the present invention.

Referring initially to FIG. 1, an EEG source 12 is illustrated which may take any of a variety of forms to provide a classic waveform of an electroencephalogram and which is commonly referred to as an EEG, the patterns or waves (cycle components) of which are useful in such medical work as diagnosis. The EEG is supplied from the source 12 to an analyzing system generally indicated at the numeral 14, which system drives a cathode ray storage 16 for developing a static display 18. As will be described in detail below, the EEG provided from the source 12 is processed to provide the display 18 in a form which is readily perceivable and which has a considerably greater information density than conventional representations. If desired, a hard-copy unit 20 may be actuated to provide a permanent record of each picture developed by the display 18.

Preliminary to considering the structure and function of the system as depicted in FIG. 1, some explanation of the format for the display 18 will be helpful. Functionally, an interval of EEG information is decoded and presented in a concentrated pictorial form indicating individual characteristics of the waves.

In accordance with tradition, a wave is considered as that portion of the waveform occurring between two bottoms or negative peaks in the EEG. On the basis of its period, a wave may be equated to frequency. The period or equivalent frequency of waves constitutes one criterion deemed important for analysis. Another important criterion for analysis involves the amplitude of the wave. The instant when a wave occurred within a sequence in also significant. To manifest such data, three-dimensional reference axes are utilized in the pictorial display 18.

In the display, each recognized wave (including spikes) is represented by an "L" character and is placed on a display or "map" according to its frequency and time of occurrence. The height of the character indicates the amplitude of the wave. All spikes are placed just to the right of a 30 hertz line to distinguish them from other waves.

Figure 2:
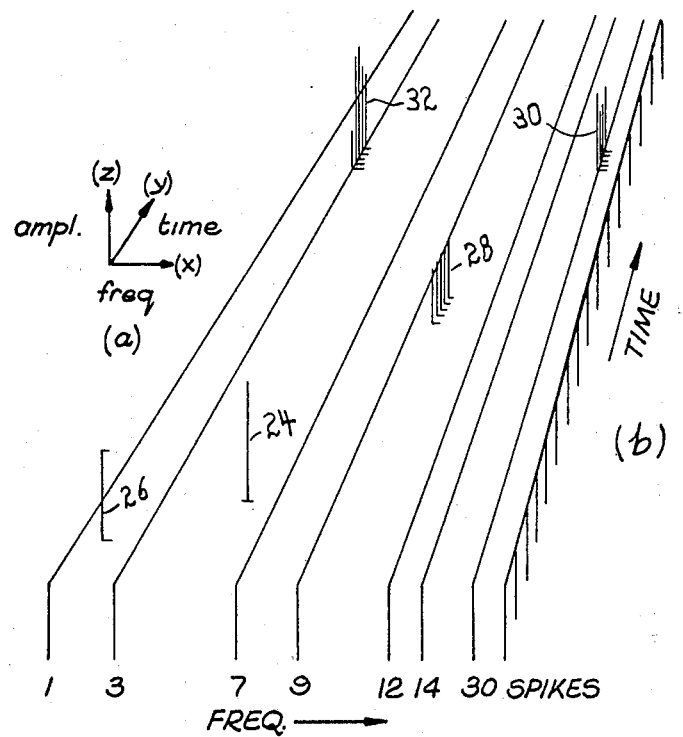
FIG. 2 is a graphic representation of a display provided by the system of FIG. 1.

Referring to FIG. 2a, a legend is illustrated indicating the significance of the three-dimensional axes in the pictorial display. The horizontal axis or abscissa (X) indicates the equivalent frequency distribution of individual waves. The vertical axis or ordinate (Z) indicates the amplitude of waves, and the third-dimension axis (Y) indicates the time of occurrence in the sequence. Thus, for analysis of a period of EEG to form a representative picture, the Y axis is scanned moving rearwardly (upwardly) in FIG. 2 as depicted and whenever a wave (or spike) is detected, an "L-shaped" representation is generated, e.g. symbol 24, in the appropriate frequency band and with a height appropriate to the amplitude of the wave. Spikes are a rather special form of waves and, as indicated above, are symbolically represented in an allotted frequency space at the right of the display.

Considering the data represented in FIG. 2, an initial wave is represented by a symbol 26, indicating that the wave occurred shortly after the beginning of the record, e.g. six seconds after beginning (t=0), and at a frequency or period of approximately two per second. Shortly thereafter, another wave represented by the symbol 24 occurred, having a sizable amplitude and a frequency approaching seven per second. Subsequently, a group 28 of symbols manifest a group of waves having an equivalent frequency of between nine and twelve per second which are closely followed by the occurrence of several spikes (indicated by the group 30) along with some low frequency waves indicated by the group 32.

Some eighty seconds of EEG is stored and manifest in the display of FIG. 2. Yet, from a single picture the observer can rapidly perceive the significant events in such a period of EEG, which by conventional analysis would require an intense study of an aperiodic waveform extending over several pages. It may therefore be seen that the system of the present invention considerably simplifies the presentation and use of EEG data.

Returning now to a consideration of FIG. 1, the systematic analysis of the EEG will be considered, first in a preliminary fashion. The EEG signal is supplied from the source 12 to an active network 34 for preliminary processing which separates the signal into three distinct components that are supplied to individual lines 36, 38, and 40.

The network 34 essentially constitutes an amplifier and filters to separate the EEG into signal components, specifically, signals containing: the so-called slow waves (1 to 8 hertz to the line 40), the fast waves (8 to 30 hertz to the line 38), and a composite signal having the potential of containing spikes (fast, large, sharp single waves to the line 36). Each of these signal components is applied to a detector circuit for sensing the occurrence of waves or waveform fragments which merit an appearance in the display 18. The line 40 is connected to a slow wave detector 46, while the line 38 is connected to a fast wave detector 44, and the line 40 is connected to a spike detector 42.

The detectors 44 and 46 provide amplitude and period (equivalent frequency) information for waves which are detected for display. As for the spike detector 42, only amplitude is manifest in the display 18. With the detection of a wave by one of the detectors 42, 44, or 46, a plurality of outputs are provided. First a trigger pulse T is supplied to indicate the occurrence of information in the waveform which is to be displayed. The trigger pulses T from the detectors 42, 44 and 46 are applied to a multiplexer 50 for subsequent application to a display generator 52.

The detectors 42, 44, and 46 also provide other information signals. Specifically, each of the detectors 42, 44, and 46 provides an amplitude signal A indicative of the amplitude of the detected wave. Furthermore, the slow wave detector 46 and the fast wave detector 44 also provide a signal F indicative of the equivalent frequency or period of the wave. As indicated, the signals A and F, along with the trigger signals T, are applied to the multiplexer 50 which also receives a signal from a calibration unit 54. Multiplexer structures are exceedingly well known in the data processing field and such structures are readily available to perform the function of the multiplexer 50 of sequencing received signals T, A, and F for application to a display generator 52 in an organized manner for driving the CRT storage 16.

Recapitulating the operation of the system of FIG. 1, the EEG waveform from the source 12 is amplified and dissected into three separate signals by the network 34 on the basis of transient frequency discrimination. Upon the occurrence of a so-called wave or significant signal component, it is detected selectively by one of the three detectors 42, 44, or 46. As a consequence, a trigger signal T is applied to the multiplexer 50 along with an amplitude signal A and (in the case of slow waves and fast waves) a signal F indicative of the frequency.

The multiplexer 50 (which includes buffer storage) supplies such signals to a display generator 52 which in turn drives the CRT storage 16 to excite a pattern component in the display 18 which will remain illuminated (in view of the storage characteristic of the display 18) for a substantial interval of time, well after a display is complete. If desired, the hard-copy unit 20, essentially a camera or copier, may then be activated to provide a record of the display 18.

Turning now to a consideration of individual components of the system of FIG. 1, the structures of the fast and slow wave detectors 42 and 44 are similar and will now be treated. Although the frequency limits imposed by these units differ, otherwise they are structurally the same.

Preliminarily, some consideration of the wave-detector function will be helpful. Essentially, the detectors 42 and 44 operate to measure the time between the two largest negative (or positive depending upon the point of view) peaks in a wave, providing that a positive peak has occurred at some time between such negative peaks. If the measured wave meets certain amplitude and duration requirements, then the measured time is converted to an equivalent frequency (the reciprocal of the period) and a recognition trigger signal is developed to command that a symbol be stored on the display 18.

Figure 3:
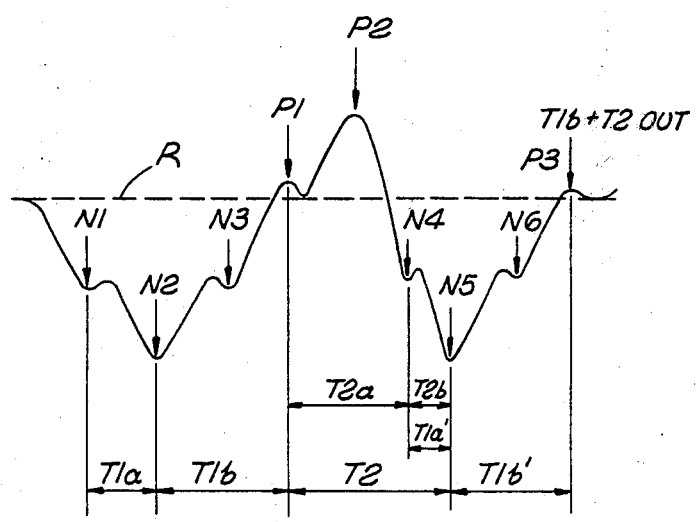
FIG. 3 is a fragment of an EEG or representative EEG waveform.

To consider the operating criteria somewhat more precisely, reference will now be made to FIG. 3 showing a fragment of an EEG as an aperiodic waveform containing a significant wave for purposes of traditional EEG analysis. The positive peaks in the waveform are designated (somewhat arbitrarily) by the letter P and a sequential number. Similarly, the negative peaks are designated by the letter N and a sequential number. Various time intervals are designated by the letter T followed by an identifier.

Considering the portion of EEG in time sequence (left to right) the first negative peak N1 could have been significant; however, with further development of the curve, it was followed by another negative peak N2 without a significant positive venture between. The interval T1a (between the peaks N1 and N2) was measured as possibly being significant; however, the data is dismissed without use.

Consideration of the EEG from the negative peak N2 indicates that a substantial wave occurs between the peaks N2 and N5. Of course, with the occurrence of the peak N2, that fact is not yet known. However, in view of the possibility of the fact, the period T1b (between the peaks N2 and P1) is measured as a possible component of the period of the wave.

As illustrated, the peak P1 is not significant as the wave shortly reverses and continues to climb upward toward the peak P2. Again, the significance of the time is uncertain; therefore, the interval T2a is measured contingent upon the further shape of the wave. As illustrated, the negative peak N4 is not significant. Consequently, the interval T2a is not significant. However, the peak N5 is significant (terminating the wave) so that the time T2 is a component of the period of the wave. It may, therefore, be seen that the wave designated between the peaks N2 and N5 has a period of T1b+T2 which period can be readily converted to an indication of the equivalent frequency by taking the reciprocal of the value. As will be explained with respect to the operating structure, a signal indicative of the period T1b+T2 is provided as an output signal at the time of the positive peak P3 as illustrated.

Figure 4:
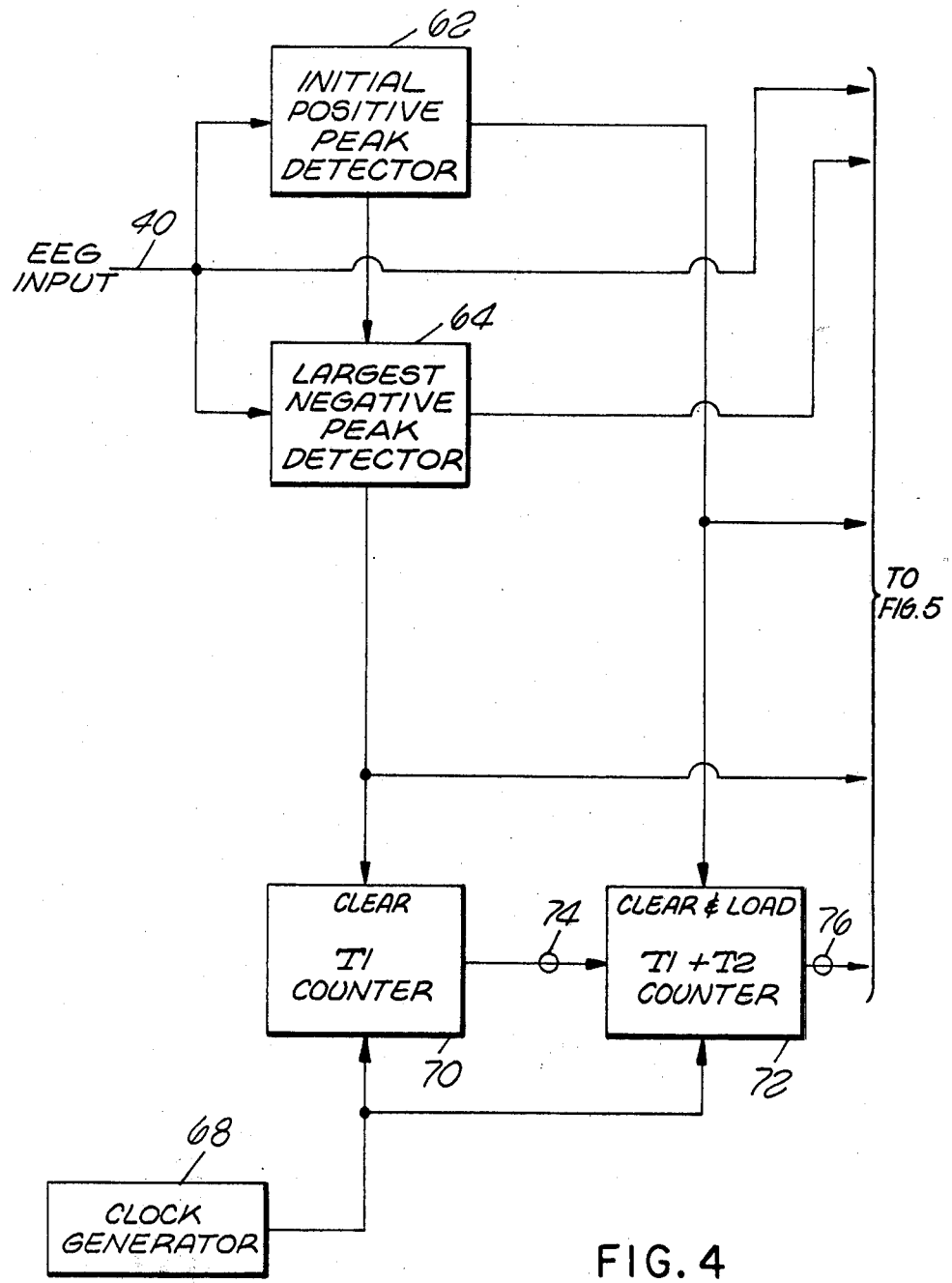
FIGS. 4 and 5 taken together show a block diagram of a portion of the system of FIG. 1.
Figure 5:
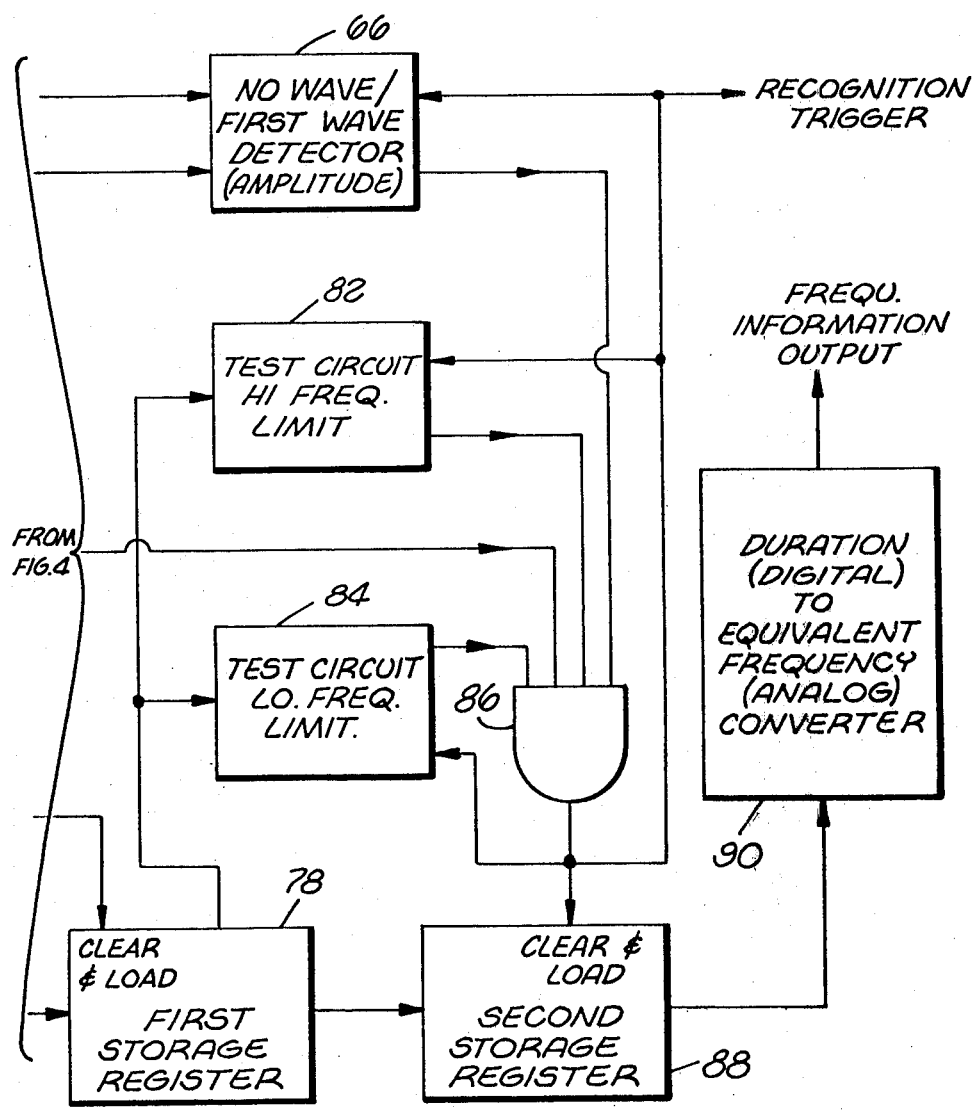

Pursuing the explanation of the detectors for sensing waves (as analytically described above with respect to FIG. 3), consideration will now be directed to the composite block diagram of FIGS. 4 and 5. The preliminarily processed EEG (slow-wave component or input to the slow wave detector, shown in FIGS. 4 and 5) appear on a line 40 which is connected to a number of blocks representing functional circuits. The line 40 is connected to three amplitude detectors 62, 64, and 66. Each of these detectors functions to form a pulse (high level of a binary signal) upon detecting a particular occurrence in the amplitude of the received EEG component. The detector 62 is a positive peak detector and functions to provide pulses that manifest positive peaks, e.g. peaks P1, P2, P3 and so on as shown in FIG. 3. The detector 64 manifests negative peaks, as the peaks N1, N2, N3, and so on (FIG. 3). Forms of both such circuits are well known and widely used in the art.

Generally, the detectors 62 and 64 sense or detect the occurrence of a wave as illustrated in FIG. 3 by controlling counters (described below) which serve to indicate the duration of such a wave. As explained in greater detail below, the detector 66 monitors amplitude variations serving to reject components of the waveform which components do not attain sufficient amplitude variation to qualify as a wave.

The measurement of wave periods is based on the operation of a clock generator 68 (lower left) which provides uniformly spaced clock pulses to a pair of counters 70 and 72. The counter 70 is reset or cleared upon each occurrence of a negative peak N, as sensed by the detector 64. Upon the occurrence of a positive peak (sensed by the detector 62), the contents of the counter 70 is transferred into the counter 72 which resumes counting from the received value. The count in the counter 70 will be designated as inteval I1 while the incremental interval added to the interval I1 registered in the counter 72 will be designated interval I2.

Although the action may not be significant (depending on the following portion of the waveform) upon the detection of a negative peak by the detector 64, the contents of the counter 72, indicating an interval I1+I2 is transferred through a cable 76 to a register 78 upon receiving a command pulse from the negative-peak detector 64. The contents of the register 78 conditionally indicates the interval or period of an observed wave.

Essentially, the wave resulting in the time interval registered in the register 78 is tested by a pair of threshold circuits for high and low time limits. Specifically, a test circuit 82 provides a high output to an "and" gate 86 if the duration or period of the potential wave indicated a frequency below a maximum limit. Somewhat similarly, the test circuit 84 provides a qualifying high binary output to the gate 86 if the duration indicates a frequency above a low limit. Intervals between such limits are partly qualified as periods of significant waves.

As indicated above, and explained in further detail below, the system of FIGS. 4 and 5 develops a value indicative of T1B plus T2 (FIG. 3) in the first storage register 78 which, if of a duration within established limits and represents a wave with an amplitude within certain limits, will be passed to a second storage register 88. Acceptance is indicated by the qualification of the gate 86 to pass signals representative of the value T1B+T2 to the second storage register 88. Concurrently, signals are also applied to reset various other components in the system, i.e. the detector 66 and the test circuits 82 and 84.

From the storage register 88, the indication of duration or period (value T1B+T2) is applied to a digital-to-analog converter 90 which provides the equivalent frequency signal F which is valid (descriptive of the wave) when the recognition trigger T is generated by the gate 86. Thus, the detector output signals T and F are developed and provided.

In view of the above structural description of the system of FIGS. 4 and 5, an exemplary operation will now be pursued to complete an understanding of the wave detectors 44 and 46. In that regard, the operation of the detector of FIGS. 4 and 5 is related to the EEG waveform as depicted in FIG. 3.

The negative peak N1 (FIG. 3) is detected to initiate counting in the counter 70 as well as to establish a test level for the wave detector 66. Of course, as there is no pattern to the waveform, as indicated above, therefore, at the time of recognition, the initial negative peak N1 may or may not be significant.

With further consideration with reference to the waveform, with the occurrence of the negative peak N2, it is apparent that N1 was in fact not significant because the wave proceeded promptly to a lower negative level. However, when the first negative peak N1 occurred, the counter 70 started and counted to a value of T1a. Then, upon the occurrence of the larger negative peak N2, the counter 70 clears or resets to begin counting (clock pulses) freshly.

Negative peak N3 is smaller than the peak N2 and, accordingly, does not result in a timing signal to the counter 70 with the consequence that the counter 70 continues counting to reach a number that represents T1b when the first positive peak P1 occurs. At that instant, the value indicative of T1b (actually time) is loaded into the counter 72 as a result of the load signal provided by the detector 62 sensing the first positive peak. The counter 72 (driven at the rate of the clock generator 68) continues to count at the same rate. Consequently, at any time after the positive peak P1 has occurred, the counter 72 contains a number which represents the total time lapsed since the last largest negative peak (e.g. N2, FIG. 3).

The value in the counter 72 is transferred to the first storage register 78 upon each occurrence of a timing signal from the negative peak detector 64. The negative peak detector 64 is reset by the first positive peak so that it starts a new cycle every time the potential changes from positive to negative.

At the instant of the negative peak N4, the value T1b+T2a is loaded into the storage register 78. However, the counter 72 continues to count undisturbed because an effective positive peak (which could load it) cannot occur while the potential is negative. After the time T2b, the number which represents an accumulation of the intervals T1b, T2a, and T2b, is transferred to the first storage register 78 (replacing the prior contents) upon the occurrence of the signal initiated by the negative peak N5 (being larger than the peak N4).

Due to the fact that the wave detectors operate in real time, they cannot anticipate whether another negative peak larger than N5 will occur to result in a wave duration longer than the period of T1b+T2 (currently stored but not used in the register 78). Therefore, the release of the value as an output is withheld. A smaller negative peak (such as N6) does not result in a timing signal and so the value in the register 78 is unchanged.

The value (T1b+T2) which represents the true duration of the wave (portion of the waveform between negative peak N2 and negative peak N5) is finally transferred to the storage register 88 upon the occurrence of a signal provided from the first positive peak detector 62 responding to the positive peak P3. At that instant, since the potential is positive, no related negative peak could occur and therefore the wave is indicated to have been completed. Simultaneously with loading the correct wave-duration value in the storage register 88, digital-to-analog conversion is initiated and a recognition trigger signal is delivered to the display system indicating that the analog form of the value T1b+T2 is available as an output.

Recapitulating to some extent, the other conditions must be satisfied to result in the final loading of the storage register 88 through the "and" gate 86; as indicated the duration stored in the register 78 must be between established high and low limits. Also, the no wave/first wave detector 66 must provide an enable pulse. That is, if a first wave occurs following an isoelectric (quiet) period, there must be at least two large negative peaks with one positive peak in between before a wave is deemed to have occurred. Thereupon, the result will be delivered on the next positive peak by the qualification of the "and" gate 86.

If a wave is correctly recognized and measured but no positive peak promptly follows, after an established time (300 to 500 milliseconds) the wave is then indicated. That is, after a time of perhaps 400 milliseconds, if the contents of the register 78 have not been released to the register 88, the detector provides a time-developed signal to accomplish the release.

From the above, it may be seen that the structure of FIGS. 4 and 5 provides the equivalent frequency signals for the slow wave detector 42 and that a similar structure may be employed as the fast wave detector 44. The separate structure for providing the amplitude signal A for each wave is distinct and will be considered in detail below. However, preliminarily, an analytical consideration with respect to FIG. 6 showing a wave (somewhat simplified from that of FIG. 3) will be helpful.

Figure 6:
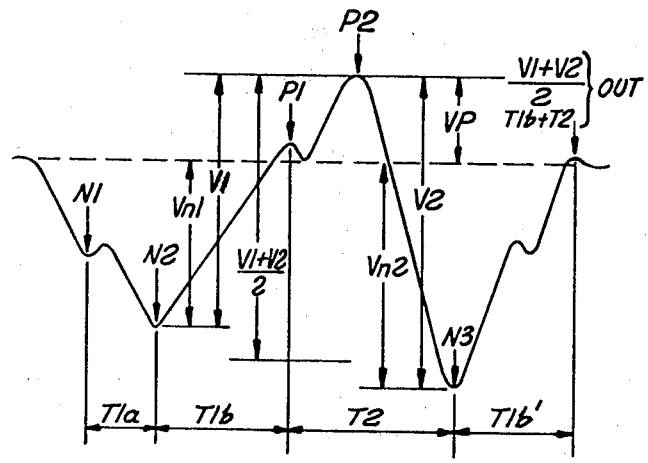
FIG. 6 is a simplified presentation of the waveform of FIG. 3.

Fundamentally, the amplitude of a wave is the semi-sum of two distinct voltages as represented in FIG. 6, i.e. V1 being the differential voltage between the first largest negative peak N2 and the largest subsequent positive peak P2. A second voltage V2 is the differential between the same positive peak P2 and the following largest negative peak N3, which essentially terminates the wave (component of the waveform designated as a wave). Generally, the demand for accuracy in EEG analysis is such as to suggest the use of analog circuits for performing the functional operation of $(V1+V2)/2$.

Figure 7:
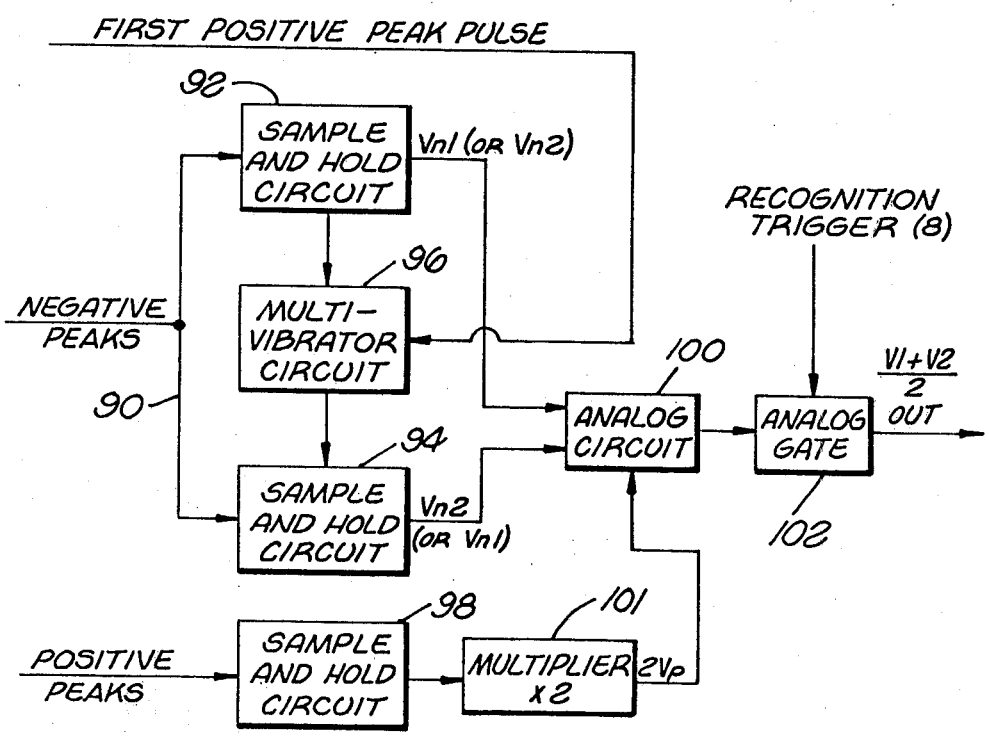
FIG. 7 is a detailed block diagram of still another portion of the system of FIG. 1.

The structure for representing the amplitude, $(V1+V2)/2$ will now be considered with reference to FIG. 7 which operates somewhat in conjunction with the structure as depicted in FIGS. 4 and 5. Specifically, negative peaks sensed by the negative peak detector 64 (FIG. 4) are applied to a line 90 (FIG. 7) which is in turn connected to sample-and-hold circuits 92 and 94 that are controlled by a flip-flop or bistable multi-vibrator 96. The positive peaks from the detector 62 (FIG. 4) are applied to a sample-and-hold circuit 98 (FIG. 7).

The sample-and-hold circuit 98 accumulates the value Vp (FIG. 6) while the sample-and-hold circuits 92 and 94 alternately accumulate the values Vn1 and Vn2. The outputs from the sample-and-hold circuits 92 and 94 are applied to an analog adder and divider circuit 100 which also receives an output from the circuit 98 through a doubler or multiplier circuit 101. The computed analog output from the circuit 100 is supplied as the desired output $(V1+V2)/2$ through an analog gate 102 which is qualified by the trigger signal T.

Considering the operation of the subsystem of FIG. 7, it is to be understood that one or the other of the sample-and-hold circuits 92 or 94 is always enabled depending upon two exclusively high qualifying signals from the flip-flop or multivibrator circuit 96. Note that both of the sample-and-hold circuits 92 and 94 receive the absolute values of negative peaks and store such values each time such a peak occurs.

For purposes of explanation, suppose that the circuit 92 is active at a time of negative peak N1 (FIG. 6) and therefore stores that value. The following peak N2 is larger and thus the amplitude value of the peak N2 will remain stored in the circuit 92 and any subsequent smaller peak does not alter it.

On the first positive peak P1, a positive peak pulse is applied to the multivibrator circuit 96 which disables the input to the circuit 92 which therefore retains the value of the peak N2, or Vn1. Concurrently, the sample-and-hold circuit 94 is enabled. During the positive phase, the sample-and-hold circuit 98 stores successively the absolute values of positive peaks; and the largest one, peak P2 having a value of Vp is registered. Consequently, the differential voltage V1 equals Vn1+Vp, which values are registered.

During the following operation, the sample-and-hold circuit 94 stores absolute values of negative peaks in the subsequent negative phase and again retains the largest one, specifically the voltage Vn2 occurring at the peak N3. Accordingly, the differential voltage V2 equals Vn2+Vp and is also available being registered in the circuits 94 and 98. The analog circuit 100 sums the voltages Vn1+Vn2+2 Vp, which from FIG. 6 can be seen analytically to equal V1+V2. The circuit 100 next divides the sum by two to produce the desired voltage $(V1+V2)/2$. That value becomes available for display upon the closing of the analog switch or gate 102 which is driven by the recognition trigger T. Concurrently, the sample-and-hold circuit 94 is again disabled while 92 is enabled as a result of altering the state of the multivibrator circuit 96.

It is to be noted that it is immaterial whether the circuit 92 or 94 is enabled first, since each operates in sequence and accordingly will store the appropriate value for the combination. It is also noteworthy that there is no need to store more than one value Vp of the largest positive peak since at the moment of display the correct value is always available. Note that a small complication may arise when the first positive peak is also the largest. The value for correct display of the amplitude of the wave in such an event is that of the previous (not the current) positive peak. To avoid error, the absolute value of positive peaks is held in a peak voltage detector (detector 62 FIG. 4) and is transferred to the sample-and-hold circuit 98 only on completion of a display.

Now, recapitulating to some extent, with reference to FIG. 1 it may be seen that the circuits have been described in detail for developing the trigger signals T, the amplitude signals A, and the equivalent frequency signals F with respect to the fast wave detector 44 and the slow wave detector 42. As for the detection of spikes, as suggested above, some specific criteria are involved which will now be considered in detail.

EEG spikes are in fact sharp waves or waveform sections of short duration (up to about 60 milliseconds) and of relatively high amplitude (25 microvolts and significantly larger). While usual EEG waves can be submitted to spectral analysis with relative ease, spikes tend to be totally lost in such analysis. Although the clinical significance of EEG spikes is well established, experts continue to debate the exact definition of a spike. If only to provide a consistent criteria for recognizing spikes, detection by automated means could result in a definite improvement in the processing and analysis of EEG data. For example, in a relatively recent study a group of five experts independently analyzed the same portion of an EEG record. One expert located 155 spikes while another located only 47. In some instances, the same spikes were not accounted for in the two analyses. Similar examples can be found throughout the history of EEG recording.

Recognizing the problems of spike definition as well as recognition, the spike detection system in the present embodiment is relatively simple and highly efficient in recognizing and displaying spikes with representative amplitude in the display and indicating the relative time of their occurrence.

Essentially, the initial or leading slope of a spike should exceed a nominal value and also should last for a predetermined time, e.g. say at least six milliseconds. If such criteria are satisfied for the leading edge, a delay is imposed to provide an observation interval, for example of thirty milliseconds. Should the signal reverse directions, have a peak, and define a minimum slope for a minimum time, say at least six milliseconds, a spike will be considered as recognized.

The disclosed structure also considers the possibility of a spike being superimposed on another wave which has a significant slope that could reduce either the leading or trailing slope of the spike. In such an event, the requirements for recognition are altered somewhat to consist of: (1) only one of the two slopes must be larger than a predetermined value; (2) the slope larger than the predetermined value must last more than six milliseconds; (3) a sharp peak must occur within a time of thirty milliseconds following the recognition of the slope which is larger than the predetermined value; and finally (4) the total amplitude of the spike must exceed 25 microvolts.

Again, recapitulating, the characteristics identifying a spike as implemented in the disclosed embodiment can be summarized as follows: (1) an amplitude of 25 microvolts or larger; (2) a duration from twelve to sixty milliseconds; (3) a sharp peak; (4) an initial leading slope larger than traditional waves; (5) a trailing slope which occurs during a six millisecond interval after the peak; (6) positive and negative slopes which last a period of time long enough to assure the signal is not spurious; and (7) smaller signals are required to be faster than large signals to be recognized as spikes; that is, as the amplitude increases, so also must the duration to qualify as a spike.

Figure 8:
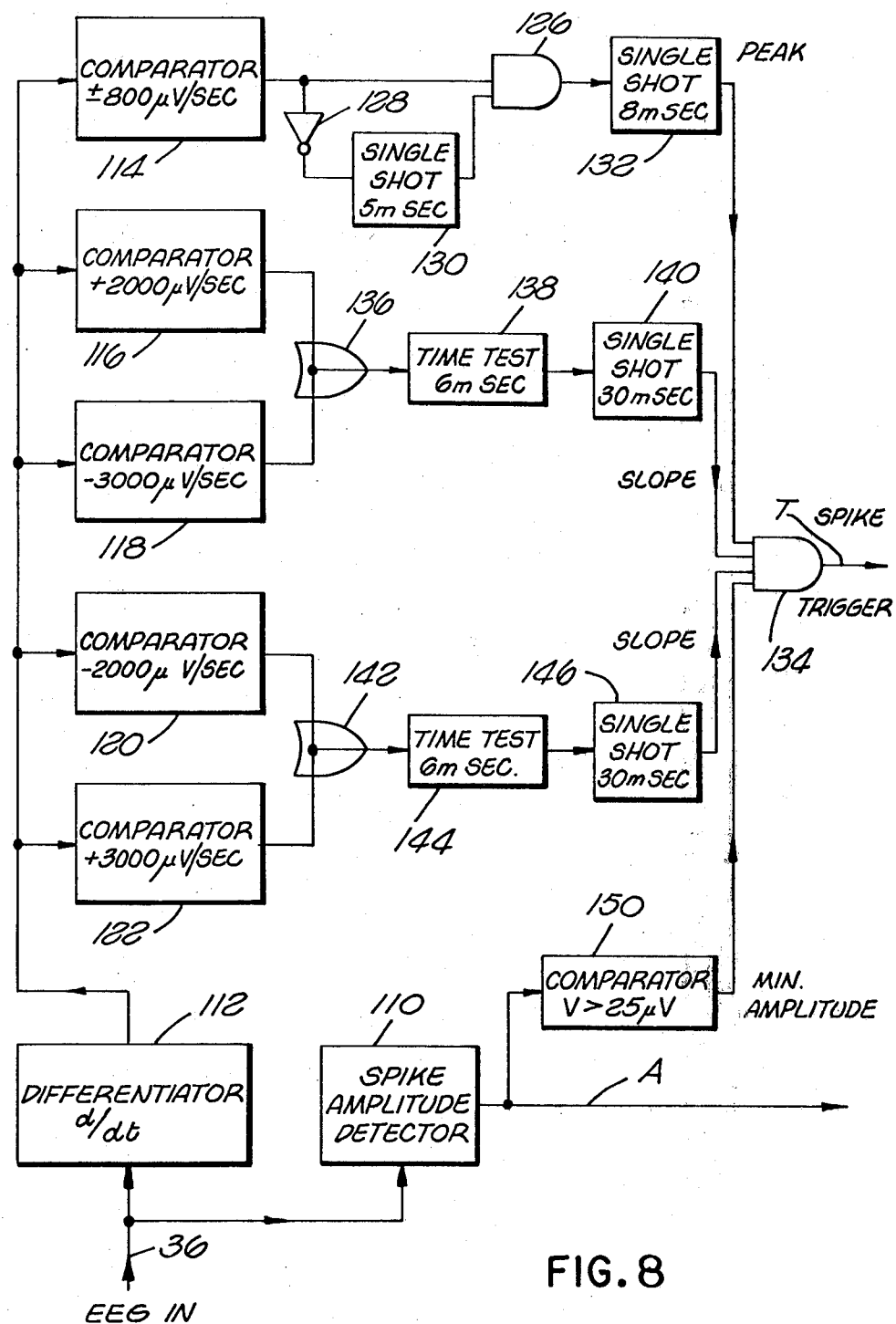
FIG. 8 is a detailed block diagram of still another portion of the system of FIG. 1.

The spike detector 46 (FIG. 1) will now be considered in detail with reference to FIG. 8 showing the input line 36 and the outputs for a spike occurrence, i.e. the amplitude signal A and trigger signal T. The spike amplitude is resolved rather directly by a spike amplitude circuit 110 which is connected to receive the EEG input directly. Essentially, the spike amplitude circuit consists of high pass filters along with rectifiers which approximate the peak voltage of the waveform even in the presence of a variety of other waves. However, the recognition of a fragment of the waveform as a spike to provide the trigger signal T is a somewhat more complex operation and utilizes a similarly more complex structure. Specifically, the EEG input signal is first differentiated by a differentiator 112, the output of which is applied to five distinct comparator circuits 114, 116, 118, 120, and 122. The comparators operate with respect to different predetermined levels of slope for the differentiated value of the EEG. For example, the comparator 114 provides a high state of a binary signal during intervals when the initial slope of the EEG exceeds 800 microvolts per second. The remaining comparator circuits function similarly with respect to increasing slope signals, however, such circuits are selectively operative with respect to signals having either a positive or a negative direction of change. Specifically, the comparator 116 provides a recognition output for slopes in excess of +2000 microvolts per second; comparator 118 provides a recognition signal for slopes in excess of −3000 microvolts per second; comparator 120 provides a recognition output for slopes in excess of −2000 microvolts per second; and comparator 122 provides a recognition output for slopes in excess of +3000 microvolts per second.

As the differentiator 112 provides an output which is proportional with the slope of the input signal, the comparators 114, 116, 118, 120, and 122 are simple amplitude or threshold circuits to provide a binary signal, the high level of which is indicative of a predetermined degree of slope in the EEG. The separate comparators are employed to enable the use of separate time-test circuits so as to accommodate the imposition of different time criteria for testing the occurrence of a spike in accordance with the standards indicated above.

The comparator 114 is connected directly to an "and" gate 126 and additionally is connected to that gate through an amplifier 128 and a single shot 130. The single shot 130 consists of a monostable multivibrator providing the low state of a binary signal as an output, except when an input triggers the single shot to provide the binary output at a high level for a predetermined interval. As designated, the interval of the single shot 130 is five milliseconds. The output from the gate 126 is provided to a single shot 132 which is in turn connected to an "and" gate 134 which supplies the trigger signal T indicative of a spike.

The comparators 116 and 118 are connected through an "or" circuit 136 to a time-test circuit 138. Functionally, the time-test circuit 138 may take the form of a delay circuit to provide an output only if the input thereto at a high level is sustained for a predetermined interval. As indicated, the time for the time-test circuit 138 is six milliseconds. The output from the time-test circuit 138 is applied to a single shot 140, the output of which is applied to the "and" gate 134.

Somewhat similar to the configuration described above, the comparators 120 and 122 are coupled through an "or" circuit 142 to a time-test circuit 144, the output of which is connected to a single shot 146 which is in turn connected to the gate 134. Finally, the "and" gate 134 also receives an input from the comparator or threshold circuit 150 which is indicative of a predetermined level of spike amplitude from the amplitude detector 110.

In view of the above structural description of the subsystem of FIG. 8, and the preliminary explanation thereof, a comprehensive understanding may now best be accomplished by assuming certain conditions and pursuing the explanation of the operation responsive to such conditions. Accordingly, assume that a positive spike is presented on the line 36. If the initial slope exceeds 2000 microvolts/sec., the signal will actuate the comparator 116 to produce a positive output for the binary signal to the time-test circuit 138. Such a signal will pass the time-test circuit 138 only if it has a duration of more than six milliseconds.

If the comparator 116 does not provide a high output for the full six milliseconds, a new cycle will be initiated as will occur each time the comparator 116 is triggered. That selectivity eliminates the effect of random noise, which is always present in an EEG signal and which is amplified by the differentiator 112. In general, such amplification cannot be avoided because low pass filtering would also alter the slope and the peak of the spike. However, short waves generated by random noise do not normally have a duration of six milliseconds and, accordingly, are discriminated in that they will not trigger the single shot 140 which initiates a 30 millisecond cycle only upon detection of an actual positive slope of a spike.

After the assumed spike has peaked, a slope more negative than −2000 microvolts/sec. must (and normally does) occur. That signal is processed through the comparator 120 and the time-test circuit 144 to trigger the single shot 146. Upon the occurrence of such a trigger, the single shot provides the high level of a binary output.

The trigger signal T is produced from the "and" gate 134 only if all four inputs to the gate are in a high state. The single shots 140 and 146 provide two of those inputs in a high state as explained above, and therefore must be set to provide high outputs during a coincident time. The longest delay between triggering the single shot 140 and the single shot 146 for the recognition of a spike is 30 milliseconds. Consequently, a symmetric spike of 60 milliseconds or less (total duration) satisfies this condition as each slope has a duration of 30 milliseconds with the consequence that both the one shots 140 and 146 are triggered with a six millisecond delay imposed by the time-test circuits 138 and 144 respectively.

Waves of greater duration (which accordingly do not qualify as spikes) will not produce the overlapped high states of the one shots 140 and 146. The shortest duration spike which still satisfies the condition described above is slightly over twelve milliseconds in duration which affords sufficient time to clear the time-test circuit 138 and upon a reversal of slope, clear the time-test circuit 144 and set the single shot 146. Limiting the range of recognition to a twelve millisecond minimum eliminates most of the false spikes or signals resulting from muscle action, e.g. EMG's.

Recapitulating to some extent, the operation described above involves four conditions to detect an EEG spike. First, the initial and final slope must exceed a predetermined level (e.g. 2000 volts/sec.) and additionally each slope must last for at least a predetermined interval, e.g. six milliseconds. In the event of a negative spike, the recognition scheme works in a similar manner as it is immaterial which of the single shots 140 and 146 is triggered initially and secondarily.

The fifth requirement of a spike to manifest detection is that it have a sharp peak which avoids false recognition of square wave or step function spurious signals or artifacts. The dual voltage comparator 114 provides a high output when a minimal slope of either signal is represented, e.g. 800 microvolts/sec.

Assume, for example, that a positive slope is provided which approaches a peak and further assume that the comparator 114 has been actuated to provide a high output. At the peak of the spike, the slope decreases below the minimum, and as a consequence, the comparator 114 ceases to provide a high output. That occurrence results in the single shot 130 being triggered as it receives an inverted form of the signal through the amplifier 128. The output from the single shot 130 remains high for five milliseconds thereby establishing the greatest permissible duration for a rounded peak in a defined spike.

Continuing with the assumed spike, further assume that the slope has now reversed and exceeds the minimum slope, e.g. −2000 microvolts/sec., during the cycle when the single shot 130 is set to provide a high output and comparator 114 again provides a high output with the result that the "and" gate 126 is qualified to trigger the single shot 132. In that situation, whenever a sharp peak occurs, the single shot 132 is set and remains in that state to provide the high output for eight milliseconds following the peak. If the single shot 140 is set at the time the peak occurs, there will be sufficient time for the single shot 146 to be triggered by the negative slope so as to qualify the "and" gate 134 with outputs by each of the single shots 132, 140, and 146. Such qualification will result in the detection of a spike providing that the sixth and last requirement is present, i.e. that the total spike amplitude is in excess of a predetermined value as qualified by the comparator 150.

Since spike-like signals of less than 25 microvolts are usually not considered significant in EEG reading, the voltage comparator 150 is set to provide a high output signal for any amplitude in excess of that level. This measurement is available at the time the other criteria have been satisfied; therefore, if the high amplitude is indicated, the gate 134 is fully qualified providing a spike recognition signal in the form of a pulse as the trigger signal T.

In addition to the operation of the spike detection as set forth above, it is also useful to detect so-called "complex" spikes which occur relatively rarely but are significant for EEG analysis. Essentially, complex spikes co-exist with waves having a relatively steep slope. Specifically, a spike may arise from the leading or trailing edge of a significant wave with the appearance of riding on the slope of the wave. Generally, the combined slope of the spike and the wave is steep on one side of the spike but diminished on the other. For example, if the spike is on the leading edge of the wave, it will have a steep leading slope, however, a relatively diminished trailing slope.

The solution to the problem of complex spike recognition is provided by the comparators 118 and 122. Specifically, assuming a spike on the leading edge of a wave, the initial slope will be well in excess of that required to actuate the comparator circuits 116 and 122 with the consequence that both the single shots 140 and 146 will be triggered. Such structure eliminates the former necessary condition for the final slope of the spike to be in excess of a predetermined slope, replacing it with a different condition that the initial slope exceed the level established by the comparator circuit 122. The other requirements remain unaltered.

Considering the complex spike which occurs on the trailing edge of a wave, the leading slope is decreased, however, the trailing slope is increased. Accordingly, the comparators 118 and 120 are triggered simultaneously to set the single shots 140 and 146. In that fashion, the complex spike is detected providing it peaks to set the single shot 132 and has sufficient amplitude to set the comparator 150.

In view of the above, it may be seen that the various criteria for detecting spikes are accommodated by the system of FIG. 8 which affords a structural form for the spike detector 46 (FIG. 1). Thus, the detectors 42, 44, and 46 have been described for providing the trigger signals T, the amplitude signals A, and in the case of non-spike waves, the equivalent frequency signals F, all to the multiplexer 50. In general, multiplexer circuits for time sequencing signals from a plurality of sources are well known in the prior art; and any of a variety of such structures may be employed. Conventionally, buffer storage is provided to accommodate the serialization of random signals. Accordingly, no detailed description of the multiplexer 50 is deemed to be appropriate herein.

Turning now to the display generator 52 (FIG. 1), some preliminary consideration is appropriate before taking up the structure of that unit as embodied in the exemplary system. As a result of the analysis, i.e. recognizing waves and determining the equivalent frequency and amplitude, waves might be displayed in a variety of patterns. However, the pattern disclosed herein offers several advantages for the present system because: three parameters (frequency, amplitude, and time) can be easily represented by the size and position of a standard symbol in an XYZ reference system; a three-dimensional system can be accurately depicted on a plane surface (CRT screen or recording paper) according to single-vanishing-point perspective; such symbolic perspective display is immediately recognizable by observers without prior training in the particular method (the display relies in general on the recognition ability of human vision); numerous symbols can be shown in a relatively small space to result in a high concentration of data in a single display; and in accordance with the present invention, the electronic processing of data for such a display is relatively simple and reliable and does not require a large computer or memory facility.

The system of the illustrative embodiment decodes the EEG information for storage and presentation in a static display while preserving individual characteristics of the wave. Each wave (including spikes) is treated as an aperiodic transistory event and defined between two successive maxima (or minima). The reciprocal of the wave duration determines the equivalent frequency as indicated above. The amplitude of each recognized wave is displayed as the height of an L-shaped character (FIG. 2) where the equivalent frequency is indicated on the horizontal and time is indicated on the basis of depth, e.g. position on the Y axis.

Figure 9:
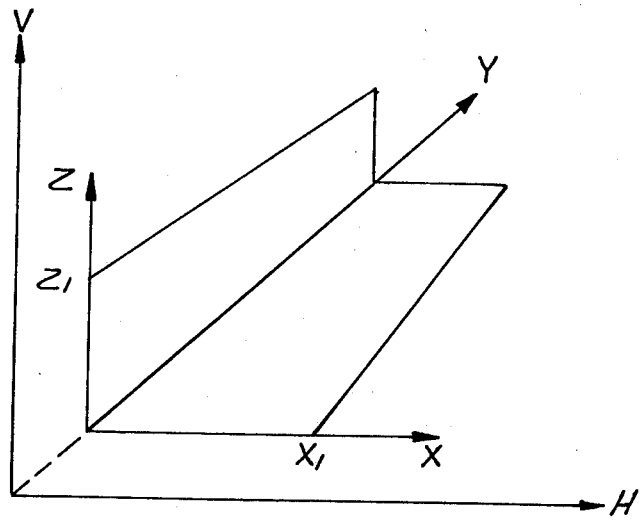
FIG. 9 is a graphic representation illustrating the display system of FIG. 1.

The principle of operation for the display generator 15 (FIG. 1) is graphically illustrated in FIG. 9. The pattern is developed as a display utilizing three axes (X for equivalent frequency; Y for time; and Z for wave amplitude). In general, the display is accomplished with the information signals described above by use of analog processing structures including operational transconductance amplifiers. Such amplifiers are basically an analog device as well known in the prior art, which function in such a manner that the gain is governed by an auxiliary voltage. Deflecting the beam along the vertical V and the horizontal H (as indicated in FIG. 9) along with beam unblanking are sufficient for representation of the virtual XYZ space as indicated in FIG. 9. The calibration for the display is provided by the calibration unit 54, such reference marks being fixed for an operation. The structure for accomplishing the EEG display (patterned in FIG. 9) is illustrated in FIG. 10 and will now be considered.

Figure 10:
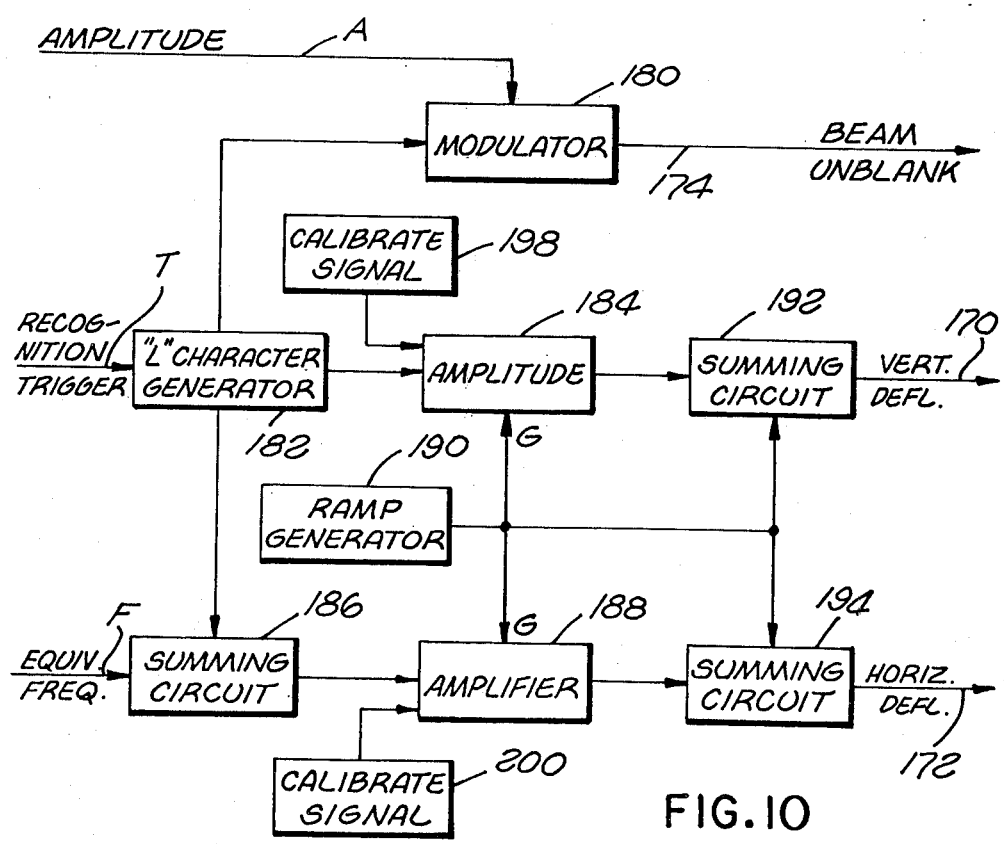
FIG. 10 is a detailed block diagram of still another portion of the system of FIG. 1.

Inputs from the multiplexer 50 (FIG. 1) are received as indicated by the system of FIG. 10, in the form of an amplitude signal A, a recognition trigger signal T, and an equivalent frequency signal F. These signals are processed to provide a vertical deflection signal on a line 170 along with a horizontal deflection signal on a line 172 and a beam unblanking signal on the line 174. The format and structure for using such signals are well known for driving a cathode ray tube display, including application to storage tubes as illustrated in FIG. 1. Specifically, the storage tube 18 accumulates portions or elements of a pattern which endure on the display 18 to ultimately develop a complete picture which may be photographed or otherwise copied. Thus, a considerable length of waveform is carried as a static representation which can be studied as a period of EEG rather than to scan the waveform otherwise recorded on multiple sheets with conventional methods.

Considering the structure of FIG. 10 in somewhat greater detail, the amplitude signal A is applied to a modulator 180 which controls the unblanking of the display beam. The modulator 180 is also connected to receive a ramp signal from a generator 182 which develops a signal for forming the L-shaped character. The generator 182 receives the recognition trigger signal T and, as explained in detail below, upon each occurrence of a trigger, formulates ramp signals.

The generator 182 is connected to apply signals to an amplifier 184 and a summing circuit 186. The equivalent frequency signal F is also applied to the summing circuit 186, the output of which is applied to an amplifier 188. The amplifiers 184 and 188 are similar, being in the form of operational transconductance amplifiers which are basically analog devices, the gain of which is determined by an auxiliary voltage, in each case supplied from a ramp generator 190 which functions on a time base related to the display. That is, the ramp generator 190 provides signals to both the amplifiers 184 and 188 and as well to summing circuits 192 and 194 which also receive inputs from the amplifiers 184 and 188 respectively. The outputs from the summing circuits 192 and 194 are to the lines 170 and 172, respectively, providing the vertical and horizontal deflection respectively.

Considering the operation of the subsystem of FIG. 10, the operational transconductance amplifiers 184 and 188 function as variable gain amplifiers working in accordance with the relationship illustrated in FIG. 9. The gain control provided from the ramp generator 190 to the amplifiers 184 and 188 is essentially a ramp which gradually and linearly reduces the gain as the vertical deflection progresses. Thus, the perspective pattern of FIG. 9 is developed.

With the above preliminary description as a background, consider now the operation of the system upon receiving drive signals. Upon each occurrence of a recognition trigger signal T, the L-shaped character generator 182 initiates an operating cycle of some 200 microseconds, during which horizontal and vertical ramp voltages are generated. These voltages do not change throughout the development of the display. The horizontal portion (foot) of all L-shaped characters is the same. The displayed height (vertically) of the L-shaped character is determined by the operation of the modulator 180 in accordance with the amplitude signal A by a variable duration unblanking of the beam accomplished as a result of the signal developed in the line 174. That is, the actual voltage ramp which generates the vertical portion of the L-shaped character remains unchanged throughout the operation; however, modulation results from turning off the beam at various heights according to the value of the amplitude signal A. Consequently, the deflection is provided for a maximum deflection on each wave occurrence; however, the beam is blanked above the proper level of the indicating vertical line.

The amplifier 184 decreases the vertical signal (of the character generator) with increasing depth in the perspective. In the process, the L-shaped character signal is added to the output of the time base in the summing circuit 192 to result in the voltage for the vertical deflection as indicated in the line 170.

The equivalent frequency signal F, which determines the position of the L-shaped character on the horizontal axis, is added with the horizontal portion (foot) of the L-shaped character in the summing circuit 186. The resulting composite signal is processed in the amplifier 188, the gain of which is determined by the depth of perspective and therefore by the time base of the instantaneous operation. A fraction of the time base voltage is then added to the processed horizontal signal in the summing circuit 194 to produce the gradual drift to the right necessary for the perspective presentation.

Thus, it may be seen that the display generator accepts the basic information in the form of the amplitude signal A, the recognition trigger T, and the equivalent frequency signal F, and produces vertical and horizontal deflection voltages plus a beam unblanking signal to define the XYZ space on the screen of a cathode ray tube and place the L-shaped characters in accordance with the format described above. It is to be noted that calibrating signals from the circuits 198 and 200 are supplied to the amplifiers 184 and 188 respectively for adjustment and calibration. Generally, such techniques are well known and widely practiced in the prior art.

In view of the above, it may be seen that a system of FIG. 1 as disclosed above will develop a static image, stored on the storage tube display 18 which is in the form described with reference to FIG. 2. Using a variety of well known structures as the hard-copy unit 20, the image or picture may be reproduced on a sheet of paper to provide a permanent record. Of course, as explained above, the picture is a considerably more perceivable form for a significant amount of EEG data. As a consequence, neurologists and other persons may perceive an analysis of the EEG by reviewing a few sheets rather than to scan through a considerable length of the EEG as a recorded waveform. Recognizing the widely varying possibilities for the utilization of structures and techniques disclosed herein, it is understood that the scope hereof should be determined in accordance with the claims as set forth below.

What is claimed is:

1. A system for recognizing and analyzing waves of an electroencephalogram manifest as an electrical signal comprising:

means adapted to receive said electrical signal for detecting peaks therein of either polarity;

means for storing the amplitude of at least one of said detected peaks of each polarity;

means for sensing a first time period lapsing between a largest peak of one polarity and a first subsequent peak of an opposite polarity;

means for sensing a second time period lapsing between said first subsequent peak and the following largest peak of said one polarity; and means for additively combining said first and second time periods to provide a wave period signal indicative of the period of a wave recognized between successive largest peaks of the same polarity separated by at least one peak of opposed polarity.

2. A system according to claim 1 to further analyze said waves comprising a means for providing a wave amplitude signal representative of the average amplitude excursion from said largest peaks to an adjacent largest peak of opposed polarity.

3. A system according to claim 2 wherein said means for amplitude measuring further includes a wave detector to detect the occurrence of waves with an amplitude below a predetermined minimum amplitude and discriminate against said waves.

4. A system according to claim 1 further including means to indicate the time of occurrence of said recognized wave by delivering a timing signal simultaneous with the occurrence of a first peak of polarity opposite to that of the largest peak which completed the recognition of said wave.

5. A system according to claim 1 wherein said system further includes means to discriminate against wave components outside predetermined period limits.

6. A system for recognition of EEG spikes manifest in an electrical signal comprising:

means for measuring the slope of voltage variations in time;

means for detecting a spike slope when said slope consistently exceeds a preset slope value for at least a predetermined period of time;

means for sensing the occurrence of a peak manifest by reversal of slope polarity within a short predetermined time; and means for delivering a signal indicative of the recognition of a spike when a detected spike slope of one polarity is followed within a predetermined time by a sensed peak and a detected spike slope of opposite polarity.

7. A system according to claim 6 further including means for measuring the amplitude of EEG spikes and for delivering a signal indicative of said amplitude simultaneous with said recognition signal.

* * * * *